United States Patent [19]

Tsuji

[11] Patent Number: 4,670,287

[45] Date of Patent: Jun. 2, 1987

[54] METHOD OF FILM-COATING HARD CAPSULES

[75] Inventor: Shinjiro Tsuji, Sakai, Japan

[73] Assignee: Washu Kirai Kogyo Kabushiki Kaisha, Sakai, Japan

[21] Appl. No.: 829,267

[22] Filed: Feb. 14, 1986

[30] Foreign Application Priority Data

Jul. 30, 1985 [JP] Japan .................................. 60-169395

[51] Int. Cl.$^4$ ................................................. A96B 6/02
[52] U.S. Cl. ........................................ 427/3; 424/463
[58] Field of Search ............................... 427/3; 424/37

[56] References Cited

U.S. PATENT DOCUMENTS 3,900,583 8/1975 Terry ........................................ 427/3
4,118,522 10/1978 Stellmach ................................ 427/3

FOREIGN PATENT DOCUMENTS 2137170 5/1971 France .................................... 424/32
0133625 11/1978 Japan ...................................... 427/3

Primary Examiner—Sam Silverberg
Attorney, Agent, or Firm—Millen & White

[57] ABSTRACT

A method of film-coating hard capsules is provided which comprises subjecting, drug-filled hard capsules to a vacuum to remove air entrapped therein and then coating the evacuated capsules while under a vacuum with a film-forming substance which is selectively soluble in the digestive juice, e.g., an enteric coating agent, e.g., hydroxypropylmethylcellulose phthalate.

12 Claims, No Drawings

METHOD OF FILM-COATING HARD CAPSULES

BACKGROUND OF THE INVENTION

1. Field of the Invention

This invention relates to a method of film-coating hard capsule. In particular, the invention relates to a method of film coating for the production of enteric hard capsule preparations.

2. Description of the Prior Art

When orally administered, pharmaceutical preparations are generally disintegrated and absorbed in the stomach. When enterically coated, however, they are not disintegrated in the stomach but are transported to the intestine, where they are disintegrated, followed by absorption of the active ingredient and production of biological or pharmacological effects thereof. In cases where an active ingredient is decomposed or denatured under acidic conditions in the stomach and as a result loses its effects or where it produces some or other adverse effect, such as gastric mucosa irritation, the troubles in question can be obviated by providing the preparations with an enteric coating. The technique of enteric coating can also be applied to the production controlled release preparations.

The enteric preparations so far frequently used generally occur as granules, tablets, and capsules filled with enteric granules. However, some drugs are not suited for tablet production by compression molding but must be made up into enteric granules or capsules filled therewith. In such case, it is required that the granules should be uniform in shape and size and so forth so that they can have satisfactory enteric and acid-resistant characteristics. To meet such requirement, much skill and a large quantity of an enteric coating material are needed. Troublesomely, varied coating conditions are to be used according to drugs differing in granule shape and size.

Accordingly, an attempt has been made to provide drug-filled hard capsules with an enteric coating to give enteric capsules (cf. Japanese Patent Publication No. 22835/69). However, since the adhesion between coating materials and hard capsules is not good, undercoating with PVP (polyvinylpyrrolidone) is necessary in using conventional enteric coating techniques. In addition, conventional coating techniques are disadvantageous in that the cap-body joint portion of capsules is incompletely coated. If enteric capsules have an incompletely coated area, disintegration would start at that area already in the gastric juice and, as a result, the original object of enteric capsules could not be attained any more.

SUMMARY OF THE INVENTION

An object of the invention is to provide perfect enteric hard capsules by solving the problems mentioned above, in particular by intensifying coating of the joint in hard capsules.

The invention thus provides a method of film-coating hard capsules which comprises coating, under vacuum, drug-filled hard capsules with a film-forming material capable of being selectively dissolved in the digestive juice.

DETAILED DESCRIPTION OF THE INVENTION

This kind of coating has so far been conducted at atmospheric pressure. In that case, the pneumatic resistance in the capsule joint portion makes it difficult for the coating solution to wet the capsule joint portion completely. It is thus difficult to perform satisfactory coating. Furthermore, since a large number of capsules are treated simultaneously, capsules are readily subjected to pressure while the coat film is not yet sufficiently dry, and accordingly the air remaining in the capsules tends to be forced out through the joint portion, whereby pinholes in the coating are easily formed.

In accordance with the invention, the whole atmosphere surrounding the capsules is evacuated, so that no pneumatic resistance is encountered in the joint portion. As a result, the joint portion is completely coated with the coating solution. Even when exposed to pressure or shock in an incompletely dried condition, pinholes will not be formed.

Unexpectedly, it has further been found that coating under vacuum results in improved adhesion between the hard capsules and the coating material. Therefore, such undercoating with PVP or the like as is proposed in Japanese Patent Publication No. 22835/69 is not necessary.

It has also been found that the capsule inside is evacuated as well and consequently the joint portion is sealed quite tightly, so that the drug in the capsules is less liable to degradation with time.

When applied to the production of enteric hard capsules, the method according to the invention can give such capsules that can 100 percent meet the requirements of the Japanese Pharmacopeia, General Tests, Disintegration Test for Enteric Preparations.

In the following, the production of enteric hard capsules is described in detail as an embodiment of the present invention.

Enteric coating agents are known and in practical use in the production of enteric tablets and enteric granules. Said agents are, for example, cellulose acetate phthalate, hydroxypropylmethylcellulose phthalate, hydroxypropylmethylcellulose acetate succinate, carboxymethylethylcellulose, methacrylic acid-methyl methacrylate copolymer and methacrylic acid-methyl acrylate copolymer, and natural products such as shellac, but are not limited to these.

The coating solution is a solution or suspension of a coating agent in a volatile solvent. If necessary, it may contain a plasticizer, a colorant, and so forth. It is also possible to give products functioning like multilayer tablets by adding to the coating solution a drug which is incompatible with the drug within capsules.

The drugs which should preferably be administered in the form of enteric preparations are those which lose their effects as a result of decomposition under gastric juice-produced acidic conditions and those which exhibit adverse effects such as gastric mucosa irritation, among others, as already mentioned hereinabove. Thus, such drugs include various vitamins, hormones, enzymes, antibiotics and chemotherapeutic agents. Among them, enzymes are mostly labile to moisture, heat and acids; such as bromelain, trypsin, chymotrypsin, serrapeptase, pancreatin, kallikrein, elstase, urokinase and other enzyme preparations. The loss of their activity is unavoidable in the process of producing granules or tablets. Therefore, they are suited for use as capsule preparations for which the production process is relatively simple. Since it is essential that said preparations should be enteric ones, the effects of the present invention are particularly remarkable when enzymes are made up into enteric capsules according to the invention.

The method of coating capsules according to the invention is the same as the conventional coating method except that the coating is performed under vacuum instead of at atmospheric pressure. Thus, hard capsules filled with a drug in the conventional manner are charged into an apparatus which enables coating under vacuum (e.g. "VG Coater" produced by K. K. Kikusui Seisakusho) and, while heating and rotating the coating pan under vacuum, the capsules are sprayed with a coating solution. The term "vacuum" as used herein need not always mean the absolute vacuum but a vacuum of the torr order is generally sufficient.

When compared with the conventional capsule preparations which comprise capsules filled with enteric granules or drug-filled capsules provided with an enteric coating in the conventional manner at atmospheric pressure, the enteric coated capsules obtained in accordance with the invention are superior in enteric and acid-resistant characteristics and more rapidly disintegrated in the simulated intestinal fluid. Furthermore, the quantities of the coating agent and so on can be reduced, the products obtained are of higher quality, and the production cost can be reduced.

Whereas the method of the invention has been described hereinabove with respect to the production of enteric coated capsules, the present invention can be applied further to the case of coating hard capsules with a coating agent soluble in the gastric juice. Thus, it is possible to endow the products with a multilayer tablet-like function by adding to the coating layer soluble in the gastric juice a drug which is incompatible with the drug within capsules. Film coating agents soluble in the gastric juice are known for use e.g. in film coating for preventing the active ingredient from being degraded due to moisture in the syrup to be used in sugar-coated plain tablets.

EXAMPLE 1

Preparation of enteric coating solution

Five (5) parts of HPMCP 200731 (hydroxypropylmethylcellulose) phthalate of the Japanese Pharmacopeia grade was dissolved in 100 parts of a 7:3 mixed solvent composed of methylene chloride and denatured ethanol, followed by addition of 1 part of glycerin fatty acid ester of the Food Additive grade to give a clear and slightly viscous enteric coating solution.

Coating of capsules

A jacketed tank in which film coating under vacuum can be performed was charged with 20,000 hard capsules each filled with 100 mg of pancreatic digestive enzyme TA (product of Amano Pharmaceutical Co., Ltd.) and the capsules within the tank were heated for 20 minutes at a jacket temperature of 50° C. under vacuum (500 torr) while revolving the tank at 0.5 rpm. Then, the vacuum was adjusted to 2 torr and the tank revolution to 20 rpm, and 10.6 kg of the above-mentioned enteric coating solution was sprayed using a one-fluid spray gun (tip orifice diameter 0.18 mm, discharge pressure 20 kg/cm$^2$).

In a typical run, spraying of the enteric coating solution resulted in a change of the vacuum from 2 torr to an equilibrated state at 9-12 torr. It took 4 hours to complete the spraying of the enteric coating solution. After spraying, the capsules were dried for 20 minutes at a jacket temperature of 50° C. and a tank revolution rate of 0.5 rpm. With the advance of drying, the vacuum returned to the original 2 torr.

The thus-obtained enteric coated capsules fully met the requirements set forth for enteric preparations in the intestinal fluid dissolution test and acid resistance test, as mentioned below.

Disintegration test

In accordance with the Japanese Pharmacopeia, General Tests, Disintegration Test for Enteric Preparations, 6 capsules were immersed in the 1st fluid and moved up and down for 120 minutes. None of the 6 capsules showed any change, such as opening, breakage or disintegration of the enteric coat film. Then, the basket was taken out gently from the 1st fluid and placed in the 2nd fluid. The capsules were disintegrated in the 2nd fluid in 10-15 minutes.

Acid resistance test

In the same manner as in the above intestinal fluid dissolution test, capsules were immersed in the 1st fluid and, after 120-minute up-and-down movement, they were taken out and cut open. The contents thus taken out were measured for the proteopeptic acitivity of pancreatic digestive enzyme TA at pH 8. The enzyme activity was 12,000 units per capsule, which was almost equal to the value before treatment with the 1st fluid.

|  | Before enteric coating | Before treatment in 1st fluid | After 120 minutes in 1st fluid |
| --- | --- | --- | --- |
| Proetopeptic activity at pH 8 (units per capsule) | 12,100 | 12,300 | 12,200 |

COMPARATIVE EXAMPLE

The same hard capsules and enteric coating solution as used in Example 1 were used.

A film coating pan (300 mm in diameter) was charged with 5,000 hard capsules. While revolving the pan at 1 rpm, the capsules were heated to 40° C. and then provided with an enteric coat by spraying 2.65 kg of the enteric coating solution through a two-fluid spray gun (orifice diameter 1.0 mm, hot air blower 1 kW), followed by drying with hot air at 50° C. for 20 minutes.

The enteric coating solution was sprayed according to the following pattern: pan revolving rate 40 rpm, spraying 15 seconds, drying 15 seconds, temperature within coating pan 40° C. The time required for the coating to be complete was 2.5 hours.

When compared in appearance with the enteric coated capsules obtained under vacuum as described above in Example 1, the enteric coated capsules obtained in this comparative example seemed to be incomplete in coating, in particular in the cap-body joint portion.

When tested according to the Japanese Pharmacopeia, General Tests, Disintegration Test for Enteric Preparations, the capsules revealed opening or breakage of the enteric coat film in the cap-body joint portion and all failed to meet the requirements.

|  | Appearance | Intestinal fluid dissolution test | |
|---|---|---|---|
|  |  | 1st fluid | 2nd fluid |
| Example 1 | A uniform coat film formed all over the capsule surface, and tight capsule-coat film adhesion. | No change after 120 minutes | Disintegration in 10–15 minutes |
| Comparative Example | Something like a bubble seen at the capsule cap-body joint. Poor coat film adhesion and the coat film ready to peel off from the capsule surface. | 5 openings and 1 breakage within 1 hour | — |

EXAMPLE 2

Capsule filling A

A homogeneous mixture of 49 g of kallidinogenase (Kallikreas "Ohkura", 9.3 IU/mg) and 100 g of lactose of the Japanese Pharmacopeia (JP) grade was uniformly mixed with a separate mixture of 1336 g of lactose of the JP grade, 730 g of corn starch of the JP grade and 45 g of talc of the JP grade. The resulting mixture was filled into capsules (orange-colored cap and white-colored body). Each capsule weighing 190.2 mg on the average (P=100) contained the following:

| Kallikreas "Ohkura", 9.3 IU/mg | 3.3 mg |
|---|---|
| Lactose JP | q.s. |
| Corn starch JP | 48.0 mg |
| Talc JP | 3.0 mg |
|  | 150.0 mg |

Capsule filling B

Kallidinogenase (Kallikreas "Ohkura", 129 IU/mg) (3.5 g) was mixed with 10 g of lactose of the JP grade, followed by addition of additional 100 g of lactose of the JP grade. After mixing to give a homogenous mixture, the mixture was uniformly mixed, as in the above case of capsule filling A, with a mixture of 1146.5 g of lactose of the JP grade, 720 g of corn starch of the JP grade, 225 g of crystalline cellulose of the JP grade (Avicel PH101, product of Asahi Chemical Industry Co., Ltd.) and 45 g of talc of the JP grade, and the resulting mixture was filled into capsules (both the cap and body being white colored). Each capsule weighed 189.7 mg on the average (P=100) and contained the following:

| Kallikreas "Ohkura", 129 IU/mg | 0.23 mg |
|---|---|
| Lactose JP | q.s. |
| Corn starch JP | 48.0 mg |
| Crystalline cellulose JP (Avicel PH101) | 15.0 mg |
| Talc JP | 3.0 mg |
|  | 150.0 mg |

Preparation of enteric coating solution

Five (5) parts of HPMCP 200731 (hydroxypropylmethylcellulose phthalate) of the JP grade is dissolved in 70 parts of a 7:3 mixed solvent composed of methylene chloride and denatured ethanol, followed by addition of 1 part of fatty acid glycerin ester of the Food Additive grade to give clear and slightly viscous enteric coating solution.

Coating of capsules

A jacketed tank in which film coating under vacuum can be conducted was charged with 10,000 capsules A and 10,000 capsules B mentioned above. The capsules within the tank were heated for 20 minutes at a jacket temperature of 50° C. under a vacuum of 500 torr while revolving the tank at 0.5 rpm. Thereafter, the vacuum was adjusted to 2 torr and the tank revolving rate to 20 rpm, and the capsules were sprayed with 6.4 kg of the above enteric contaning solution using a one-fluid spray gun (orifice dia. 0.18 mm, discharge pressure 20 kg/cm$^2$).

Upon spraying the enteric coating solution, the vacuum changed from 2 torr before spraying to 9–12 torr in an equilibrium state. The time required for spraying said quantity of the enteric coating solution was 2 hours and 20 minutes. After spraying, the capsules were dried at a jacket temperature of 50° C. and a tank revolving rate of 0.5 rpm for 10 minutes. With the advancement of drying, the vacuum returned to the original value of 2 torr.

The thus-obtained enteric capsules A or B each weighed 215.1 mg or 214.4 mg, respectively, on the average (P=100). None of them showed changes such as opening after 120-minute treatment in the first fluid for disintegration test according to the Japanese Pharmacopeia. They retained about 100 percent of the original enzyme activity. In the second fluid, they were disintegrated in 8–15 minutes. The per-capsule kallidinogenase activity data obtained are shown in the following table.

|  | Before enteric coating | Before treatment in 1st fluid | (in IU/capsule) After 120 minutes in 1st fluid |
|---|---|---|---|
| Capsule A | 30.1 | 30.3 | 29.9 |
| Capsule B | 29.9 | 29.6 | 29.8 |

What I claim is:

1. In a method of film-coating hard capsules wherein drug-filled hard capsules are coated with a film-forming substance which is selectively soluble in the digestive juice by spraying and drying a solution of the filming forming substance in a solvent onto the outer surface of the capsules, the improvement wherein the capsules are coated dried while in a chamber under vaccu sufficient to prevent pneumatic pressure from developing within the capsules during the coating process.

2. The method of claim 1, wherein the film-forming substance is an enteric-film-forming substance.

3. The method of claim 2, wherein the drug is a vitamin, hormone, enzyme or chemotherapeutic agent.

4. An enteric capsule preparation produced by the method of claim 3.

5. The method according to claim 1, comprising the further step of heating the capsules above ambient temperature in the evacuated chambe prior to initiating the coating process.

6. The method according to claim 5, wherein the capsules are heated in the evacuated chamber prior to initiating the coating process to a temperature of about 40°–50° C.

7. The method according to claim 1, wherein the chamber is maintained at a pressure of about 9–12 Torr during drying.

8. The method according to claim 5, wherein the chamber is maintained at a pressure of about 9–12 Torr during drying.

9. The method according to claim 5, wherein the chamber is a rotating tank into which the coating solution is sprayed.

10. The method according to claim 5, wherein the film forming substance is hydroxymethylcellulose phthalate.

11. The method according to claim 5, wherein the capsules are filled with an enzyme which is labile to moisture, heat and acids.

12. The method according to claim 5, wherein the enzyme is bromelain, trypsin, chymotrypsin, serrapeptase, pancreatin, kallikrein, elstase or urokinase.

* * * * *

UNITED STATES PATENT AND TRADEMARK OFFICE
CERTIFICATE OF CORRECTION

PATENT NO. : 4,670,287

DATED : June 2, 1987

INVENTOR(S) : Shinjiro Tsuji

It is certified that error appears in the above-identified patent and that said Letters Patent is hereby corrected as shown below:

Column 6, Claim 1, Line 46:

reads "juice by spraying and drying a solution of the filming"

should read --juice by spraying and drying a solution of the film- --

Column 6, Claim 1, Line 49:

Reads "coated dried while in a chamber under vaccu sufficient"

should read --coated dried while in a chamber under vacuum sufficient--

Column 6, Claim 5, Line 60:

Reads "perature in the evacuated chambe prior to initiating the"

should read --perature in the evacuated chamber prior to initiating the--

Signed and Sealed this

Fifteenth Day of September, 1987

Attest:

DONALD J. QUIGG

Attesting Officer      Commissioner of Patents and Trademarks